(12) United States Patent
Martin-Lomas et al.

(10) Patent No.: US 6,939,857 B2
(45) Date of Patent: *Sep. 6, 2005

(54) COMPOUNDS AND THEIR USES (75) Inventors: Manuel Martin-Lomas, Seville (ES); Thomas William Rademacher, Oxford (GB); Hugo Norberto Caro, London (GB); Irene Francois, Housell Woking (GB)

(73) Assignee: Rodaris Pharmaceuticals Limited, Oxfordshire (GB)

( * ) Notice: Subject to any disclaimer, the term of this patent is extended or adjusted under 35 U.S.C. 154(b) by 335 days.

This patent is subject to a terminal disclaimer.

(21) Appl. No.: 09/798,125

(22) Filed: Mar. 2, 2001

(65) Prior Publication Data

US 2001/0053767 A1 Dec. 20, 2001

Related U.S. Application Data (60) Provisional application No. 60/203,607, filed on May 12, 2000.

(51) Int. Cl.$^7$ .................. A61K 31/70; C07G 11/00; C07H 15/00

(52) U.S. Cl. .................. 514/25; 536/4.1; 536/17.2; 536/18.4

(58) Field of Search ................... 536/4.1, 17.2, 536/18.4, 55.1, 123.1; 514/25, 54, 62

(56) References Cited

U.S. PATENT DOCUMENTS

| | | |
|---|---|---|
| 5,268,272 A | 12/1993 | Mullner et al. |
| 5,395,828 A | 3/1995 | Schiebler et al. |
| 5,550,166 A | 8/1996 | Ostlund et al. |
| 5,652,221 A | 7/1997 | Larner et al. |
| 6,004,938 A | 12/1999 | Frick et al. |

FOREIGN PATENT DOCUMENTS

| | | | |
|---|---|---|---|
| EP | 0 520 372 A1 | 12/1992 | |
| JP | 63196596 | 8/1988 | |
| JP | 03237101 | 10/1991 | |
| JP | 04120089 | 4/1992 | |
| JP | 06293790 | 10/1994 | |
| WO | WO 96/14075 | 5/1996 | |
| WO | WO 98/10791 | 3/1998 | |
| WO | WO 98/11116 | 3/1998 | |
| WO | WO 98/11117 | 3/1998 | |
| WO | WO 98/11435 | 3/1998 | |
| WO | WO 98/50049 | 11/1998 | |
| WO | WO 99/06421 | 2/1999 | |
| WO | WO 99/38516 | 8/1999 | |
| WO | WO 99/06421 | * 11/1999 | ......... C07H/15/207 |
| WO | WO 00/15254 | 3/2000 | |
| WO | WO 00/39141 | 7/2000 | |

OTHER PUBLICATIONS

Schweizer et al, J. Sci. Food. Agric. 1978, 29(2), 148–154.*
Arthur Crossman et al "Synthesis of same second generation substrate analogues of early intermediates in the biosynthetic pathway of glycophosphatidylinositol membrane anchors", 1999, vol. 321, pp 42–51.*
Robert Plourde et al "synthesis of Potentially Insulin Mimetic Phosphodisaccharide", 1990, vol. 31, No. 19, pp. 2693–2696.*
Fernandez De La Pradilla, R. et al., "Improved preparation of acetals of myo–inositol and its (±)–1–benzyl ether: conformational analysis of di–O–isopropylidene–myo–inositol derivatives"; Carbohydrate Research, 207: 249–257 (1990).
Bernabé, M. et al., "Chiral recognition of 1–O–allyl and 1–O–benzyl–D– and –L– myo–inositol by cyclomaltohexaose and –heptaose (α–and β–cyclodextrin)"; Carbohydrate Research, 208: 255–259 (1990).
Zapata, A. et al., "Novel Highly Regioselective O–Alkylation and O–Acylation of myo–Inositol"; J. Org. Chem., 56: 444–447 (1991).
Jaramillo, C. et al., "Synthesis of 1D–1,2–anhydro–myo-inositol"; Carbohydrate Research, 209: 296–298 (1991).
Jaramillo, C. et al., "Approaches to the Synthesis of Glycosyl Phosphatidyl Inositols. Enantioselective Synthesis of Optically Active chiro– and myo–Inositols."; Tetrahedron Letters, 32(22): 2501–2504 (1991).
Vasella, A. et al., "194. Convenient Synthesis of 2–Azido–2–deoxy–aldoses by Diazo Transfer"; Helvetica Chimica Acta, 74: 2073–2077 (1991).
Aguiló, A. et al., "The Regioselective Synthesis of Enantiomerically Pure myo–Inositol Derivatives. Efficient Synthesis of myo–Inositol 1,4,5–trisphosphate."; Tetrahedron Letters, 33(3): 401–404 (1992).
Zapata, A. et al., "Builing blocks for the synthesis of glycosyl–myo–inositols involved in the insulin intracellular signalling process"; Carbohydrate Research, 234: 93–106 (1992).
Caro, H. et al., "Synthesis and insulin–like activity of phosphorylated galactose derivatives"; Carbohydrate Research, 240: 119–131 (1993).
Singh, K. et al., "Synthesis of Oligosaccharides Structurally Related to E–Selectin Ligands"; J. Chem. Soc., Chem. Commun., 775–776 (1994).

(Continued)

*Primary Examiner*—James O. Wilson
*Assistant Examiner*—Ganapathy Krishnan
(74) *Attorney, Agent, or Firm*—Dann, Dorfman, Herrell & Skillman, P.C.

(57) ABSTRACT

Compounds having a mimetic or antagonistic property of an inositol phosphoglycan, and the uses of these compounds are disclosed, together with the use, e.g. to treat a condition ameliorated by administration of an IPG second messenger or an IPG antagonist thereof. Preferred compounds of the invention are based on the substituted cyclitols, such as the chiro-inositol derivative pinitol (3-O-methyl-chiro-inositol).

25 Claims, 4 Drawing Sheets

OTHER PUBLICATIONS

Chiara, J.L. et al., "A Stereoselective Route to Enantiomerically Pure myo–Inositol Derivatives Starting from D–Mannitol"; Tetrahedron Letters, 35(18): 2969–2972 (1994).

Zapata, A. et al., "Synthesis and investigation of the possible insulin–like activity of 1D–4–O–and 1D–6–O–(2–amino–2–deoxy–β–D–glucopyranosyl)– myo–inositol 1–phosphate and 1D–6–O–(2–amino–2–deoxy–α–D– glucopyranosyl)–myo–inositol 1,2–(cyclic phosphate)"; Carbohydrate Research, 264: 21–31 (1994).

Jaramillo, C. et al., "An Effective Strategy for the Synthesis of 6–O–(2–Amino–2–deoxy–α–D–glucopyranosyl)–D–chiro– and –D–myo–inositol 1–Phosphate Related to Putative Insulin Mimetics"; J. Org. Chem., 59: 3135–3141 (1994).

Varela–Nieto, I. et al., "Cell Signalling by Inositol Phosphoglycans from Different Species"; Comp. Biochem. Physiol., 115B(2): 223–241 (1996).

Martin–Lomas, M. et al., "The solution conformation of glycosyl inositols related to inositolphosphoglycan (IPG) mediators"; Tetrahedron: Asymmetry, 11: 37–51 (2000).

Baeschlin, D.K. et al., "1,2–Diacetals in Synthesis: Total Synthesis of a Glycosylphosphatidylinositol Anchor of *Trypanosoma brucei*"; Chem. Eur. J., 6(1): 172–186 (2000).

Frick, W. et al., "Structure–Activity Relationship of Synthetic Phosphoinositolglycans Mimicking Metabolic Insulin Action"; Biochemistry, 37(38): 13421–13436 (1998).

Jaworek, C.H. et al., "Synthesis of an Inositol–Containing Trisaccharide Related to Insulin Signal Transduction"; Tetrahedron Letters, 40: 667–670 (1999).

Deeg, M.A. et al., "Inositol Glycan Phosphate Derived from Human Erythrocyte Acetylcholinesterase Glycolipid Anchor and Inositol Cyclic 1,2–Phosphate Antagonize Glucagon Activation of Glycogen Phosphorylase"; Diabetes, 42(9): 1318–1323 (1993).

Güther, M.L.S. et al., "Molecular species analysis and quantification of the glycosylphosphatidylinositol intermediate glycolipid C from *Trypsanosoma brucei*"; Mol. Biochem. Parasitol., 77(2): 137–145 (1996).

Mayer, T.G. et al., "Glycosyl Phosphatidylinositol (GPI) Anchor Synthesis Based on Versatile Building Blocks—Total Synthesis of a GPI Anchor of Yeast"; Eur. J. Org. Chem. 1153–1165 (1999).

Müller, G. et al., "Phosphoinositolglycan–Peptides from Yeast Potently Induce Metabolic Insulin Actions in Isolated Rat Adipocytes, Cardiomyocytes, and Diaphragms"; Endocrinology, 138: 3459–3475 (1997).

Baeschlin, D.K. et al., "Rapid Assembly of Oligosaccharides: Total Synthesis of a Glycosylphosphatidylinositol Anchor of *Trypanosoma brucei*"; Angew. Chem. Int. Ed., 37(24): 3423–3427 (1998).

Derappe, C. et al., "Characterization of a New Oligosaccharide Containing myo–Inositol Found in Pregnancy Urine"; Carbohydrate Research, 115: 221–229 (1983).

Angyal, S.J. et al., "Cyclitols. Part XXII. Synthesis of Some Mannosyl– and Mannosyl–mannosyl–myoinositols, and of Galactinol"; J. Chem. Soc. (C), 433–438 (1966).

Reddy, K.K. et al., "Insulin Second Messengers: Synthesis of 6–O–(2–Amino–2–deoxy–α–D–glucopyranosyl)–D–chiro–inositol–1–phosphate"; Tetrahedron Lets., 34(49): 7869–7872 (1993).

Plourde, R. et al., "Synthesis of a Potentially Insulin–Mimetic Phosphodisaccharide", Tetrahedron Lets., 31(19): 2693–2696 (1990).

Stralfors, P., "Insulin second messengers"; Bioessays, 19: 327–335 (1997).

Field, M.C., "Is there evidence for phospho–oligosaccharides as insulin mediators?"; Glycobiology, 7: 161–168 (1997).

Jones, D.R. et al., "The role of glycosyl–phosphatidylinositol in signal transduction"; Int. J. Biochem. Cell Biol., 30: 313–326 (1998).

Mato, J.M. et al., "Partial Structure of an Insulin–Sensitive Glycophospholipid"; Biochem. Biophys. Res. Commun., 146: 764–770 (1987).

Larner, J., "Rat Liver Insulin Mediator Which Stimulates Pyruvate Dehydrogenase Phosphatase Contains Galactosamine and D–Chiroinositol"; Biochem. Biophys. Res. Commun., 151: 1416–1426 (1988).

Caro, H.N. et al., "Isolation and Partial Characterisation of Insulin–Mimetic Inositol Phosphoglycans from Human Liver"; Biochem. Mol. Med., 61: 214–228 (1997).

Gigg, R. et al., "Synthesis of Glycosylphosphatidylinositol Anchors"; in "Glycopeptides and Related Compounds"; Large & Warren, Eds., Marcel Dekker, New York, 327–392 (1997).

Corey, E.J. et al., "Protection of Hydroxyl Groups as tert-Butyldimethylsilyl Derivatives"; J. Am. Chem. Soc., 94: 6190–6191 (1972).

Ley, S.V. et al., "Cyclohexane–1,2–diacetals (CDA): A New Protecting Group for Vicinal Diols in Carbohydrates"; Angew. Chem. Int. Ed. Engl., 33: 2290–2292 (1994).

Kinzy, W. et al., "Synthese des Trisaccharids aus der 'Repeating Unit' des Kapselpolysaccharids von *Neisseria meningitidis* (Serogruppe L)"; Liebigs Ann. Chem., 1537–1545 (1985).

Schmidt, R.R. et al., "Anomeric–Oxygen Activation for Glycoside Synthesis: The Trichloroacetimidate Method"; Adv. Carbohydr. Chem. Biochem. 50: 21–123 (1994).

Rademacher, T.W. et al., "Inositolphosphoglycan second messengers"; Brazilian J. Med. Biol. Res., 27: 327–341 (1994).

Murakata, C. et al., "Stereoselective total synthesis of the glycosyl phosphatidylinositol (GPI) anchor of *Trypanosoma brucei*"; Carbohydrate Research, 235: 95–114 (1992).

Martin–Lomas, M. et al., "Inositolphosphoglycan Mediators Structurally Related to Glycosyl Phosphatidylinositol Anchors: Synthesis, Structure and Biological Activity"; Chem. Eur. J., 6(19): 3608–3621 (2000).

Ruda, K. et al., "Synthesis of an Inositol Phosphoglycan Fragment found in Leishmania Parasites"; Tetrahedron, 56(24): 3969–3975 (2000).

Dietrich, H. et al., "Glycosyl Inositol Derivatives Related to Inositolphosphoglycan Mediators: Synthesis, Structure, and Biological Activity"; Chem. Eur. J., 5(1): 320–336 (1999).

Smith, T.K. et al., "Parasite and mammalian GPI biosynthetic pathways can be distinguished using synthetic substrate analogues"; The EMBO Journal, 16(22): 6667–6675 (1997).

Fankhauser, C. et al., "Structures of Glycosylphosphatidylinositol Membrane Anchors from *Saccharomyces cerevisiae*"; J. Biol. Chem., 268(35): 26365–26374 (1993).

Menon, A.K. et al., "Cell–free Synthesis of Glycosyl–phosphatidylinositol Precursors for the Glycolipid Membrane Anchor of *Trypanosoma brucei* Variant Surface Glycoproteins"; J. Biol. Chem., 265(16): 9033–9042 (1990).

Sakata, K. et al., "2–O–(β–L–Arabinopyranosyl)–myo–inositol as a Main Constituent of Tea (*Camellia sinensis*)"; Agric. Biol. Chem., 53(11): 2975–2979 (1989).

Gorin, P.A.J. et al., "Formation of O–β–D–Glucopyranosyl– and O–β–D–Galactopyranosyl–Myo–Inositols by Glycosyl Transfer"; Can. J. Chem., 43(8): 2259–2264 (1965).

Quemener, B. et al., "Ciceritol, A Pinitol Digalactoside from Seeds of Chickpea, Lentil and White Lupin", Phytochemistry, 22(8): 1745–1751 (1983).

Carter, H.E. et al., "Biochemistry of the Sphingolipids. XVIII. Complete Structure of Tetrasaccharide Phytoglycolipid"; Biochemistry, 8(1): 383–388 (1969).

Wait, R. et al., "Strategies for the structure determination of parasite glycoconjugates using fast atom bombardment mass spectrometry"; Cienc. Cult. (Sao Paulo), 46(4): 255–261 (1994).

Previato, J.O. et al., "Structural Characterization of a Novel Class of Glycophosphosphingolipids from the Protozoan *Leptomonas samueli*"; J. Biol. Chem., 267(34): 24279–24286 (1992).

Hsieh, T.C.Y. et al., "Glycophosphoceramides from Plants—Purification and Characterization of a Novel Tetrasaccharide Derived from Tobacco Leaf Glycolipids"; J. Biol. Chem., 256(15): 7747–55 (1981).

Wait, R. et al., "Structure Determination of Phosphoinositol Oligosaccharides from Parasitic Protozoa Using Fast Atom Bombardment Mass Spectrometry"; Org. Mass Spectrom., 29(12): 767–781 (1994).

Smith, C.K. et al., "α–D–Mannopyranosyl–(1→4)–α–glucuronopyranosyl–(1→2)–myo–inositol, a new and unusual oligosaccharide from cultured rose cells"; Phytochemistry, 52: 387–396 (1999).

Ley, S.V. et al., "Microbial Oxidation in Synthesis: Preparation of a Potential Insulin Mimic from Benzene"; Synlett, 12: 997–998 (1992).

Crossman, Jr., A. et al., "Synthesis of some second generation substrate analogues of early intermediates in the biosynthetic pathway of glycosylphosphatidylinositol membrane anchors"; Carbohydrate Research, 321(1–2): 42–51 (1999).

Crossman, Jr. A. et al., "Parasite glyconjugates. Part 7. Synthesis of further substrate analogues of early intermediates in the biosynthetic pathway of glycosylphosphatidylinositol membrane anchors"; J. Chem. Soc., Perkin Trans. 1: 2769–2774 (1997).

Smith, T.K. et al., "Substrate Specificity of the Dolichol Phosphate Mannose: Glucosaminyl Phosphatidylinositol α1–4–Mannosyltransferase of the Glycosylphosphatidylinositol Biosynthetic Pathway of African Trypanosomes"; J. Biol. Chem., 271(11): 6476–6482 (1996).

Cottaz, S. et al., "Parasite glycoconjugates. Part 3. Synthesis of substrate analogues of early intermediates in the biosynthetic pathway of glycosylphosphatidylinositol membrane anchors"; J. Chem. Soc. Perkin Trans. 1: 1673–1678 (1995).

Smith, T.K. et al., "Parasite–Specific Inhibition of the Glycosylphosphatidylinositol Biosynthetic Pathway by Stereoisometric Substrate Analogues"; Biochemistry, 39: 11801–11807 (2000).

Morris, J.C. et al., "Glycan Requirements of Glycosylphosphatidylinositol Phospholipase C from *Trypanosoma brucei*"; J. Biol. Chem., 270(6): 2517–2524 (1995).

Kunjara, S. et al., "Tissue Specific Release of Inositol Phosphoglycans"; Biopolymers and Bioproducts: Structure, Function and Applications, 301–306 (1995).

Khiar, N. et al., "Strategies for the Synthesis of Inositol Phosphoglycan Second Messengers"; Carbohydrate Mimics, Concepts and Methods, Chapleur Ed. Wiley VCH, 443–462 (1998).

* cited by examiner

COMPOUNDS AND THEIR USES

CROSS REFERENCE TO RELATED APPLICATION(S)

This application claims the benefit of U.S. Provisional Application No. 60/203,607, filed May 12, 2000, the entire disclosure of which is incorporated by reference in this application.

FIELD OF THE INVENTION

The present invention relates to compounds and their uses, and in particular to compounds which have a mimetic or antagonistic property of an inositol phosphoglycan, and the uses of these compounds, e.g. to treat a condition ameliorated by administration of an IPG second messenger or an IPG antagonist thereof

BACKGROUND OF THE INVENTION

Many of the actions of growth factors on cells are thought to be mediated by a family of inositol phosphoglycan (IPG) second messengers[13]. It is thought that the source of IPGs is a "free" form of glycosyl phosphatidylinositol (GPI) situated in cell membranes. IPCs are thought to be released by the action of phosphatidylinositol-specific phospholipases following binding of growth factors to receptors on the cell surface. There is evidence that IPGs mediate the action of a large number of growth factors including insulin, nerve growth factor, hepatocyte growth factor, insulin-like growth factor I (IGF-I), fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland.

Partially characterised inositolphosphoglycans (IPGs) have been postulated to mediate the action of a number of growth factors including insulin and insulin-like growth factor I (IGF-I)[1]. Despite their isolation from several tissues type, the precise chemical structures of these IPGs are, however, still unknown and two main structural groups have been proposed on the basis of the chemical composition[2,3] which display different biological activity and tissue distribution[4]; the family of glucosamine-myo-inositol containing IPGs (IPG-A) and the family of chiro-inositol-galactosamine containing IPGs (IPG-P).

In an attempt to establish the minimal structural requirements for biological activity, a number of compounds containing some of the basic structural motifs that have been postulated for IPG mediators have been synthesised in the art[5]. These synthetic compounds include O-(2-amino-2-deoxy-D-glucopyranosyl)-α(1-6)-chiro-inositol 1-phosphate and O-(2-amino-2-deoxy-D-glucopyranosyl)-α (1-6)-myo-inositol 1-phosphate[6].

U.S. Pat. No 6,004,938 (Hoechst) discloses a group of synthetic inositol glycans having insulin-like action. The compounds are based on 2–6 monsaccharide units linked to an inositol moiety. The examples in the patent all employ myo-inositol and are composed of 5 or 6 units apart from two pseudo-trisaccharide compounds G and H. Compounds G and H are HO—PO(H)O-6Man-α(1-4)-GluN-α(1-6)-(L) inositol-1,2(cyclic) phosphate and HO—PO(H)O-6Man-α (1-4)-GluN-α(1-6)-(L)inositol, otherwise known as O-(6-hydrogenphosphonate-α-D-mannopyranosyl)-(1-4)-(2-amino-2-deoxy-α-D-glucopyranosyl)-(1-6)-L-myo-inositol-1,2-cyclic phosphate and O-(6-hydrogenphosphonate-α-D-mannopyranosyl)-(1-4)-(2-amino-2-deoxy-α-D-glucopyranosyl)-L-myo-inositol. The properties of exemplified compounds are investigated in lipogenesis and glucose transport assays employing rat fat cells.

WO96/14075 (University of Virginia) discloses a generic family of compounds D-hexosamines linked to an inositol via a β1,4-linkage. The inositols can be myo or chiro-inositol or pinitol, while the hexosamines are glucosamine or galactosamine. However, this application describes the synthesis of just two compounds 4-O-(2-deoxy-2-amino-β-D-galactopyranosyl)-D-pinitol and 4-O-(2-deoxy-2-amino-β-D-galactopyranosyl)-D-chiro-inositol, or in IUPAC notation O-(2-amino-2-deoxy-β-D-galactopyranosyl)-(1-4)-D-pinitol and O-(2-amino-2-deoxy-β-D-galactopyranosyl)-(1-4)-D-chiro-inositol.

WO99/06421 (University of Virginia) describes synthetic insulin mimetic substances and includes a general formula I showing β1,4-linked disaccharides. However, despite this the compounds synthesised in this application are exactly the same as those disclosed in the applicant's earlier application, WO96/14075.

A multi-step synthesis of a IPG-P mimetic from glucose has been previously reported in Jaramillo et al[6], which discloses a compound called C4, 1D-6-O-(2-amino-2-deoxy-α-D-glucopyranosyl)-chiro-inositol-1-phosphate. A further synthesis of this compound is described in our co-pending International Patent Application PCT/GB99/03715 (Rademacher Group Limited).

It remains a significant problem in the art to produce synthetic compounds which can mimic one or more of the activities of inositol phosphoglycans or which act as antagonists of IPGs.

SUMMARY OF THE INVENTION

Broadly, the present invention relates to IPG mimetic and antagonist compounds, and in particular to compounds based on the substituted cyclitols such as the chiro-inositol derivative pinitol (3-O-methyl-chiro-inositol). It also relates to methods of producing the compounds and to their medical uses. The compounds disclosed herein are useful as synthetic mimetics of IPG-P or IPG-A second messengers and/or growth factors whose action is mediated by IPGs, or a competitive antagonists of IPGs.

Accordingly, in a first aspect, the present invention provides a compound represented by the general formula:

X-substituted cyclitol wherein:
X represents a sugar residue;
the cyclitol is substituted at the 3-position with a substituted or unsubstituted alkyl group;
the sugar residue and cyclitol are linked other than at position 3 of the cyclitol, wherein the linkage is an α or β linkage other than a β1,4 linkage; and,
the sugar residue is unsubstituted or substituted with one and four groups, and the cyclitol is unsubstituted or is further substituted with between one and four groups, the group or groups being independently selected from:
(a) phosphoryl groups such as phosphate —O—P(O)(OH)$_2$; thiophosphate-O—P(S)(OH)$_2$; phosphate esters —O—P (O)(OR)$_2$; thiophosphate esters —O—P(S)(OR)$_2$, phosphonate —O—P(O)OHR; thiophosphonate —O—P(S) OHR; substituted phosphonate —O—P(O)OR$_1$R$_2$; substituted thiophosphoinate —O—P(S)OR$_1$R$_2$; —O—P (S)(OH)(SH); cyclic phosphate;

(b) other phosphorus containing compounds such as phosphoramidite —O—P(OR)—NR$_1$R$_2$ and phosphoramidate —O—P(O)(OR)—NR$_1$R$_2$;

(c) sulphur groups such as —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide —NHSO$_2$NH$_2$;

(d) amino groups such as —NHR, —NR$_1$R$_2$, —NHAc, —NHCOR, —NH—O—COR, —NHSO$_3^-$; —NHSO$_2$R, —N(SO$_2$R)$_2$, and/or amidino groups such as —NH—C(=NH)NH$_2$ and/or ureido groups such as —NH—CO—NR$_1$R$_2$ or thiouriedo groups such as —NH—C(S)—NH$_2$;

(e) hydroxy groups and substituted hydroxy groups such as —OR$_3$, where R$_3$ is C$_{1-10}$ unsubstituted or substituted alkyl, e.g. CHF$_2$ or CF$_3$, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or where two hydroxyl groups are joined as a ketal;

(f) halogen substituents such as fluorine or chlorine;

(g) hydrogen, e.g. to provide a deoxy sugar.

wherein R, R$_1$ and R$_2$ are independently hydrogen or C$_{1-10}$ unsubstituted or substituted alkyl or aryl.

The compounds may be provided as racemic or diastereomeric mixtures, resolved or partially resolved optical isomers, and as pharmaceutically acceptable salts, esters and derivatives as discussed in more detail below.

Preferably, the sugar residue is a hexose or a pentose, and may be an aldose or a ketose. The sugar residue can be a member of the D or L series and can include amino sugars, deoxy sugars and their uronic acid derivatives. Preferably, where the sugar residue is a hexose, it is selected from the group consisting of glucose, galactose or mannose, or substituted hexose sugar residues such as an amino sugar residue such as hexosamine, galactosamine or glucosamine, and more preferably D-glucosamine (2-amino-2-deoxy-D-glucose) or D-galactosamine (2-amino-2-deoxy-D-galactose). Preferred pentose sugar residues include arabinose, fucose and ribose. The sugar residue is optionally substituted at one, two, three or four positions, other than anomeric position or the position of linkage to the cyclitol moiety.

The cyclitol can be the D or L enantiomer. The alkyl group at the 3-position of the cyclitol is preferably C$_{1-10}$ alkyl, and may be a substituted or unsubstituted primary, secondary or tertiary alkyl group. Examples of substituted groups include CF$_3$, X(CH$_2$)$_n$—O— (where X is hydrogen, or substituted or unsubstituted alkyl), CHF$_2$O—. A preferred alkyl group is methyl when the cyclitol is D or L-pinitol (3-O-methyl-chiro-inositol), and is optionally substituted at one or more of the positions other than the 3-position or the position of linkage to the sugar residue. In further embodiments, the cyclitol may have one or more of the hydroxyl groups through which the substituents described above are removed so that any substituent(s) are linked to the ring carbon atom. The cyclitol moiety is optionally further substituted at one, two, three or four positions, other than the position of linkage to the sugar residue.

Preferably, the linkage position of the sugar residue to the cyclitol is selected from a 1,1 linkage, 1,2 linkage or 1,5 linkage or 1,6 linkage. The linkage between the units is preferably via one of the oxygen atoms of the cyclitol moiety. However, this oxygen atom can be replaced one or more times by —CH$_2$— or —S— groups.

In a preferred embodiment, the present invention provides a compound represented by the general formula:

$$X\text{-}1,6\text{-pinitol}$$

wherein,

X represents a sugar residue;

the sugar residue is unsubstituted or substituted with between one and four groups, and the pinitol is unsubstituted or is further substituted with between one and four groups, the group or groups being independently selected from:

(a) phosphoryl groups such as phosphate —O—P(O)(OH)$_2$; thiophosphate —O—P(S)(OH)$_2$; phosphate esters —O—P(O)(OR)$_2$; thiophosphate esters —O—P(S)(OR)$_2$; phosphonate —O—P(O)OHR; thiophosphonate —O—P(S)OHR; substituted phosphonate —O—P(O)OR$_1$R$_2$; substituted thiophosphonate —O—P(S)OR$_1$R$_2$, —O—P(S)(OH)(SH); cyclic phosphate;

(b) other phosphorus containing compounds such as phosphoramidite —O—P(OR)—NR$_1$R$_2$ and phosphoramidate —O—P(O)(OR)—NR$_1$R$_2$;

(c) sulphur groups such as —O—S(O)(OH), —SH, —SR, —S(—O)—R, —S(O)$_2$R, RO—S(O)$_2^-$, —O—SO$_2$NH$_2$, —O—SO$_2$R$_1$R$_2$ or sulphamide —NHSO$_2$NH$_2$;

(d) amino groups such as —NHR, —NR$_1$R$_2$, —NHAc, —NHCOR, —NH—O—COR, —NHSO$_3^-$, —NHSO$_2$R, —N(SO$_2$R)$_2$, and/or amidino groups such as —NH—C(=NH)NH$_2$ and/or ureido groups such as —NH—CO—NR$_1$R$_2$ or thiouriedo groups such as —NH—C(S)—NH$_2$;

(e) hydroxy groups and substituted hydroxy groups such as —OR$_3$, where R$_3$ is C$_{1-10}$ unsubstituted or substituted alkyl, e.g. CHF$_2$ or CF$_3$, alkoxyalkyl, aryloxyalkyl, cycloalkyl, alkenyl (unsubstituted alkyl), alkylene (C$_{3-7}$ cycloalkyl), —OCOR, aryl, heteroaryl, acetal, or where two hydroxyl groups are joined as a ketal, (f) halogen substituents such as fluorine or chlorine;

(g) hydrogen, e.g. to provide a deoxy sugar.

wherein R, R$_1$ and R$_2$ are independently hydrogen or C$_{1-10}$ unsubstituted or substituted alkyl or aryl.

These compounds may be either α1,6 or β1,6 linked, and examples showing the synthesis of these compounds are provided in the description below. The synthesis of compounds 1–4, bearing the glucosaminyl α and β 1-6 (1, 2) and the galactosaminyl α and β 1-6 (3, 4) structural motifs from 3-O-methyl-D-chiro-inositol (D-pinitol) is reported below. Examples of α-linked compounds of the invention are compounds RGL1024 and 1025, the synthesis of which is described in detail below. Examples of β-linked compounds of the invention are compound RGL1015, the synthesis of which is described in detail below, and compound RGL1119.

In preferred embodiments, the present invention provides a compound selected from the group consisting of RGL1015, RGL1024, RGL1025 and RGL1119, and substituted forms and derivatives thereof as defined above.

RGL1015 O-(2-amino-2-deoxy-D-glucopyranosyl)-β(1,6)-D-3-O-methyl-chiro-inositol.

RGL1024 O-(2-amino-2-deoxy-D-glucopyranosyl)-α(1,6)-D-3-O-methyl-chiro-inositol.

RGL1025 O-(2-amino-2deoxy-D-galactopyranosyl)-α(1,6)-D-3-O-methyl-chiro-inositol.

RGL1191 1'-D-6-O-(2'-amino-2'-deoxy-β-D-galactopyranosyl)-3-O-methyl-D-chiro-inositol, In a further aspect, the present invention provides methods for making the compounds of the invention or their intermediates as set out in the following experimental description and the schemes. In a further related aspect, the present invention further relates to compounds which are the novel intermediates described herein.

In a further aspect, the present invention provides one or more of the above compounds for use in a method of medical treatment. The compounds may be useful as IPG mimetics or IPG antagonists, e.g. competitive antagonists.

In a further aspect, the present invention provides the use of one or more of the above compounds for the preparation of a medicament for the treatment of a condition ameliorated by the administration of an inositol phosphoglycan (IPG) second messenger or an IPG antagonist. Examples of such conditions are set out in the pharmaceutical uses section below.

In a further aspect, the present invention provides a method of treating a condition in a mammal ameliorated by an inositol phosphoglycan (IPG) second messenger or an IPG antagonist, the method comprising administering to the mammal a therapeutically effective amount of one or more of the above compounds.

Embodiments of the invention will now be described by way of example and not limitation with reference to the accompanying drawings.

DETAILED DESCRIPTION

Inositol Phosphoglycans (IPGs)

IPG-A mediators modulate the activity of a number of insulin-dependent enzymes such as cAMP dependent protein kinase (inhibits), adenylate cyclase (inhibits) and cAMP phospho-diesterases (stimulates). In contrast, IPG-P mediators modulate the activity of insulin-dependent enzymes such as pyruvate dehydrogenase phosphatase (stimulates) and glycogen synthase phosphatase (stimulates), The A-type mediators mimic the lipogenic activity of insulin on adipocytes, whereas the P-type mediators mimic the glycogenic activity of insulin on muscle. Both A-and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle, brain, adipose, heart) and bovine liver IPG-A and IPG-P biological activity has also been detected in human liver and placenta, malaria parasitized (BC and mycobacteria. The ability of an anti-inositolglycan antibody to inhibit insulin action on human placental cytotrophoblasts and BC3H1 myocytes or bovine-derived IPG action on rat diaphragm and chick cochleovestibular ganglia suggests cross-species conservation of many structural features. However, it is important to note that although the prior art includes these reports of IPG-A and IPG-P activity in some biological fractions, the purification or characterisation of the agents responsible for the activity is not disclosed.

IPG-A substances are cyclitol-containing carbohydrates, also containing $Zn^{2+}$ ions and phosphate and having the properties of regulating lipogenic activity and inhibiting cAMP dependent protein kinase. They may also inhibit adenylate cyclase, be mitogenic when added to EGF-transfected fibroblasts in serum free medium, and stimulate lipogenesis in adipocytes.

IPG-P substances are cyclitol-containing carbohydrates, also containing $Mn^{2+}$ and/or $Zn^{2+}$ ions and phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase Methods for obtaining A-type and P-type mediators are set out in Caro et al, 1997, and in WO98/11116 and WO98/11117. Protocols for determining characteristic IPG biological activities such as PDH activation, PKA inhibition, acetylCoA activation, fructose-1,6-bisphosphatase activity and lipogenesis are well known in the art, e.g. as described in Caro et al[14].

Drug Formulation

The compounds of the invention may be derivatised in various ways. As used herein "derivatives" of the compounds includes salts, coordination complexes with metal ions such as $Mn^{2+}$ and $Zn^{2+}$, esters such as in vivo hydrolysable esters, free acids or bases, hydrates, prodrugs or lipids, coupling partners, and protecting groups.

Salts of the compounds of the invention are preferably physiologically well tolerated and non toxic. Many examples of salts are known to those skilled in the art. Compounds having acidic groups, such as phosphates or sulfates, can form salts with alkaline or alkaline earth metals such as Na, K, Mg and Ca, and with organic amines such as triethylamine and Tris (2-hydroxyethyl)amine. Salts can be formed between compounds with basic groups, e.g. amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives which as prodrugs of the compounds are convertible in vivo or in vitro into one of the parent compounds. Typically, at least one of the biological activities of compound will be reduced in the pro drug form of the compound, and can be activated by conversion of the prodrug to release the compound or a metabolite of it. An example of prodrugs are glycolipid derivatives in which one or more lipid moieties are provided as substituents on the sugar residue or the cyclitol moiety, leading to the release of the free form of the compound by cleavage with a phospholipase enzyme. Examples of prodrugs include the use of protecting groups which may be removed in situ releasing active compound or serve to inhibit clearance of the drug in vivo. Protecting groups are well known in the art and are discussed further below. An example of a suitable protecting group that might be used as a prodrug is the azido group used in the synthesis below, e.g. on the 2-position of the sugar moiety.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

Pharmaceutical Compositions

The compounds described herein or their derivatives can be formulated in pharmaceutical compositions, and administered to patients in a variety of forms, in particular to treat conditions which are ameliorated by the administration of inositol phosphoglycan second messengers or IPG antagonists such as competitive antagonist.

Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parental administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parentally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight The composition may further comprise one or more other pharmaceutically active agents, either further compounds of the invention, inositol phosphoglycans, growth factors such as insulin, NGF or other growth factors listed below, or other drugs, e.g. those in use for the treatment of diabetes or other conditions set out below.

Medical Uses

As set out above, IPGs are second messengers for a range of different growth factors, including insulin, nerve growth factor, hepatocyte growth factor, insulin-like growth factor I (IGF-I). fibroblast growth factor, transforming growth factor β, the action of IL-2 on B-cells and T-cells, ACTH signalling of adrenocortical cells, IgE, FSH and hCG stimulation of granulosa cells, thyrotropin stimulation of thyroid cells, cell proliferation in the early developing ear and rat mammary gland. Consequently, IPGs or their antagonists can be used in the treatment or amelioration of disorders mediated by the growth factors or to mimic specific growth factor biological activities.

Examples of conditions which can be treated using IPG or IPG antagonists include diabetes, obesity, pre-eclampsia, neurotrophic disorders, hepatic damage and adrenal atrophy.

WO98/10791 discloses that pre-eclampsia is characterised by elevated levels of IPG-P and that it can be treated using an IPG-P antagonist. Compounds of the invention which are IPG-P antagonists, e.g antagonists which compete with wild-type IPG-P but lack one or more of its activities, could be used in the treatment of pre-eclampsia.

The use of both IPG-P and IPG-A and IPG-A antagonists in the diagnosis and treatment of diabetes is disclosed in WO98/11435. This application discloses that in some forms of diabetes the ratio of P:A-type IPrs is imbalanced and can be corrected by administering a medicament containing an appropriate ratio of IPG-P, IPG-A or antagonist(s) thereof. In particular, it describes the treatment of obese type II diabetes (NIDDM) patients with a P-type IPG and/or an A-type IPG antagonist and the treatment of IDDM or lean type II diabetes (body mass index <27) with a mixture of P- and A-type IPGs, typically in a P:A ratio of about 6:1 for males and 4:1 for females. The compounds and compositions of the present invention can be employed in such types of treatment, More particularly, the compounds are likely to be of use in the treatment of various form of diabetes and diabetic complications including diabetes due to insulin resistance, insulin resistance in type I diabetes and brittle diabetes, obese or lean type II diabetes, and of conditions associated with insulin resistance or insulin underproduction, such as neurotrophic disorders or polycystic ovary syndrome, lipodystrophy, age-related memory loss, and post-ischaemic damage secondary to stroke or post-transplant complications.

The compounds of this invention are also likely to be of use in controlling neuron proliferation or neurite outgrowth, either in vitro or in vivo, e.g. acting as a nerve or neurite growth factor mimetic second messenger. They may thus have applications in the treatment and/or diagnosis of any condition related to neuron proliferation or neurite differentiation. WO99/38516 discloses that IPG-A and synthetic mimetics thereof cause neuron proliferation, mimicking the action of the growth factor IGF-I. In contrast, IPG-P and synthetic mimetics thereof such as compound C4 cause neurite outgrowth. The neurons may be central (brain and spinal cord) neurons, peripheral (sympathetic, parasympathetic, sensory and enteric) neurons, or motor neurons. Treatments may involve the treatment of damage to nerve, spinal cord or central nervous system damage secondary to trauma, or autoimmune or metabolic damage, or postischaemic damage secondary to stroke or post-transplant complications, motor neuron disease, neurodegenerative disorders or neuropathy. Damage to the nervous system includes the results of trauma, stroke, surgery, infection (e.g. by viral agents), ischemia, metabolic disease, toxic agents, or a combination of these or similar causes. Motor neuron disease includes conditions involving spinal muscular atrophy, paralysis or amyotrophic lateral sclerosis. Neurodegenerative disorders include Parkinson's disease, Alzheimer's disease, epilepsy, multiple sclerosis, Huntingdon's chorea and Meniere's disease.

The compounds of the invention may also be useful as hepatocyte growth factor mimetic second messengers, e.g, in the preparation of medicaments for the treatment of hepatic damage caused by infection, alcohol abuse, drug sensitivity, or autoimmunity. The compounds may also be useful as fibroblast growth factor mimetic second messengers or epidermal growth factor mimetic second messengers, e.g in the preparation of medicaments for the promotion of wound healing following surgery or trauma or tissue damage induced by ischaemia or autoimmunity.

In other embodiments, the compounds of the invention may be useful as adrenal cell growth factor mimetic second messengers or ACTH mimetic second messengers in the preparation of a medicament for the treatment of disease states involving adrenal atrophy.

Methods of Making the Compounds

Based on the disclosure herein, the knowledge in the art and in references[5-11] the skilled person could couple sugar residues and cyclitols together, optionally with one or more substituents. By way of example, compound RGL1119 was made in this way.

Useful guidance on the synthesis of the exemplified compounds and for introducing the substituents set out herein is provided by the papers by Gigg & Gigg, Khiar & Martin-Lomas[5] and Baeschlin et al[6] and the references cited therein.

Phosphoryl groups such as phosphate, cyclic phosphate or substituted phosphate or cyclic phosphate can be substituted into the compounds of the invention by the phosphate or phosphoramidite method, Bannwath et al, Helvetica Chemice Acta, 70:175–186, 1987 and Yu & Fraser-Reid, Tetrahedron Lett., 29:979–982, 1988.

Phosphate protecting groups can also be synthesized according to the methods disclosed in Hoeben-Weyl, Methods of Organic Chemistry, volume 12/1 or 12/2, Teilheimer, Synthetic Methods of Organic Chemistry, Vol 45. Protecting groups for the OH of sugars include menthoxycarbonyl (MntCO), acetal (in particular, two R groups may together represent a bridging acetal such as O-cyclohexylidene, O-isopropylidene or O-benzylidene), tert-butyldimethylsilyl (TBDMS), benzyl (Bn), tert-butyldiphenylsilyl (TBDPS). Many protecting groups suitable for use in the syntheses and reactions of saccharides are known and are well documented in standard reference works. The choice depends in part on the route by which the compound is synthesised and/or on the uses to which it is to be put, including the reactions which it is subsequently intended to undergo Bioactivity Assays The compounds of the invention can be tested for one or more the characteristic IPG-P and/or IPG-A activities mentioned above to determine whether they will be suitable for use a IPG mimetics or antagonists. Preferred assays measure the effect of the compounds on PDH phosphatase, PKA or lipogenesis. Protocols for these assays are provided in Caro et al[14].

EXAMPLES

General Methods

All reactions were carried out under an atmosphere of dry argon using oven-dried glassware and freshly distilled and dried solvents. THF and diethyl ether were distilled from sodium benzophenone ketyl. Dichloromethane and acetonitrile were distilled from calcium hydride. TLC was performed on Silica gel $GF_{254}$ (Merck) with detection by charring with phosphomolibdic acid/EtOH. For flash chromatography, Silica Gel (Merck 230–400 mesh) was used. Columns were eluted with positive air pressure. Chromatographic eluents are given as volume to volume ratios (v/v). Routine NMR spectra were recorded with Bruker Avance DPX300 ($^1$H, 300 MHz), Bruker Avance DRX400 ($^1$H, 400 MHz), and Bruker Avance DRX500 ($^1$H, 500 MHz) spectrometers. Chemical shifts are reported in ppm, and coupling constants are reported in Hz. Spectra were referenced to the residual proton or carbon signals of the solvent. High-resolution mass spectra were recorded on a Kratos MS-80RFA 241-MC apparatus.

Figure 1:
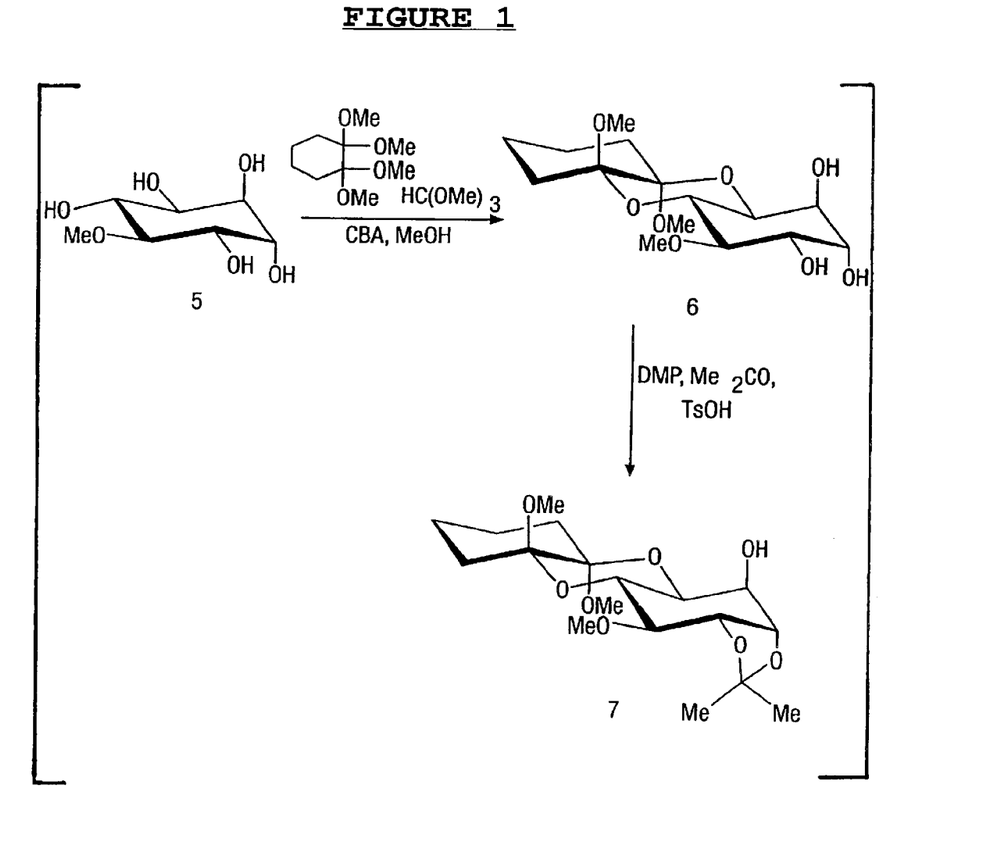
FIG. 1 shows a reaction scheme (Scheme 1) for the synthesis of building block 7 by bis-protection of the trans-diequatorially oriented hydroxyl groups of D-pinitol 5 as cyclohexane 1,2-diacetal and the cis-oriented hydroxyl groups as isopropylidene acetal.

Optical rotations were determined with a Perkin-Elmer 341 polarimeter. Elemental analyses were performed using a Leco CHNS-932 apparatus. The organic extracts were dried over anhydrous sodium sulfate and concentrated in vacuo The synthesis of compounds 1–4 involved the preparation of a glycosyl acceptor with position 6 differentiated to be reactive with the corresponding glycosyl donor. Protection of the pinitol unit as cyclohexane-1,2-diacetal as proposed by Ley[8] was attempted. The selectivity of the reaction of 5 with 1,1,2,2-tetramethoxycyclohexane arises from the stabilising influence of the four anomeric effects in the resulting acetal 6 and the equatorial arrangement of all four sterically demanding alkyl substituents of the central 1,4-dioxane unit (Scheme 1). Treatment of 6 with 2,2-dimethoxypropane in the presence of TsOH gave 7 in 80% yield.

Figure 2:
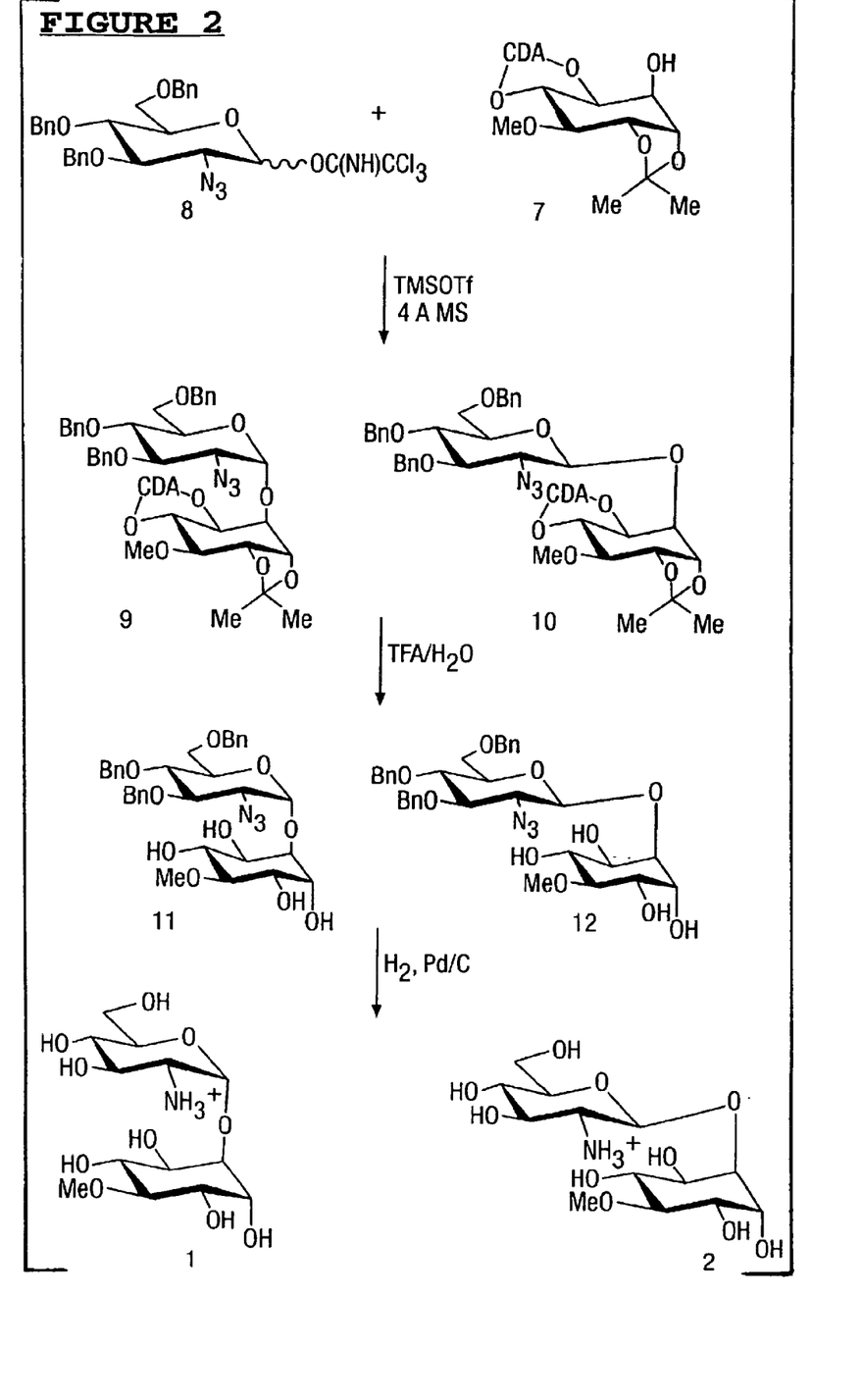
FIG. 2 shows a reaction scheme (Scheme 2) for the glycosylation of D-pinitol building block 7 with the 2-azido-2-deoxy-D-glucopyranosyl trichloroacetimidate 8 to give the IPG-like compounds 1 and 2.

Glycosylation of 7 with 2-azido-2-deoxy-3,4,6-tri-O-benzyl-D-glucopyransol-trichloroacetimidate 8[9] prepared following a well established procedure[10,6b], in dichloromethane and using TMSOTf as promoter[11] gave a 2:1 mixture of the α (9) and β (10) linked pseudodisaccharides in 54% yield (Scheme 2). The acetal groups were removed [12] to give 11 and 12 respectively which were subjected to hydrogenolysis to afford finally 1 and 2 in quantitative yield.

Figure 3:
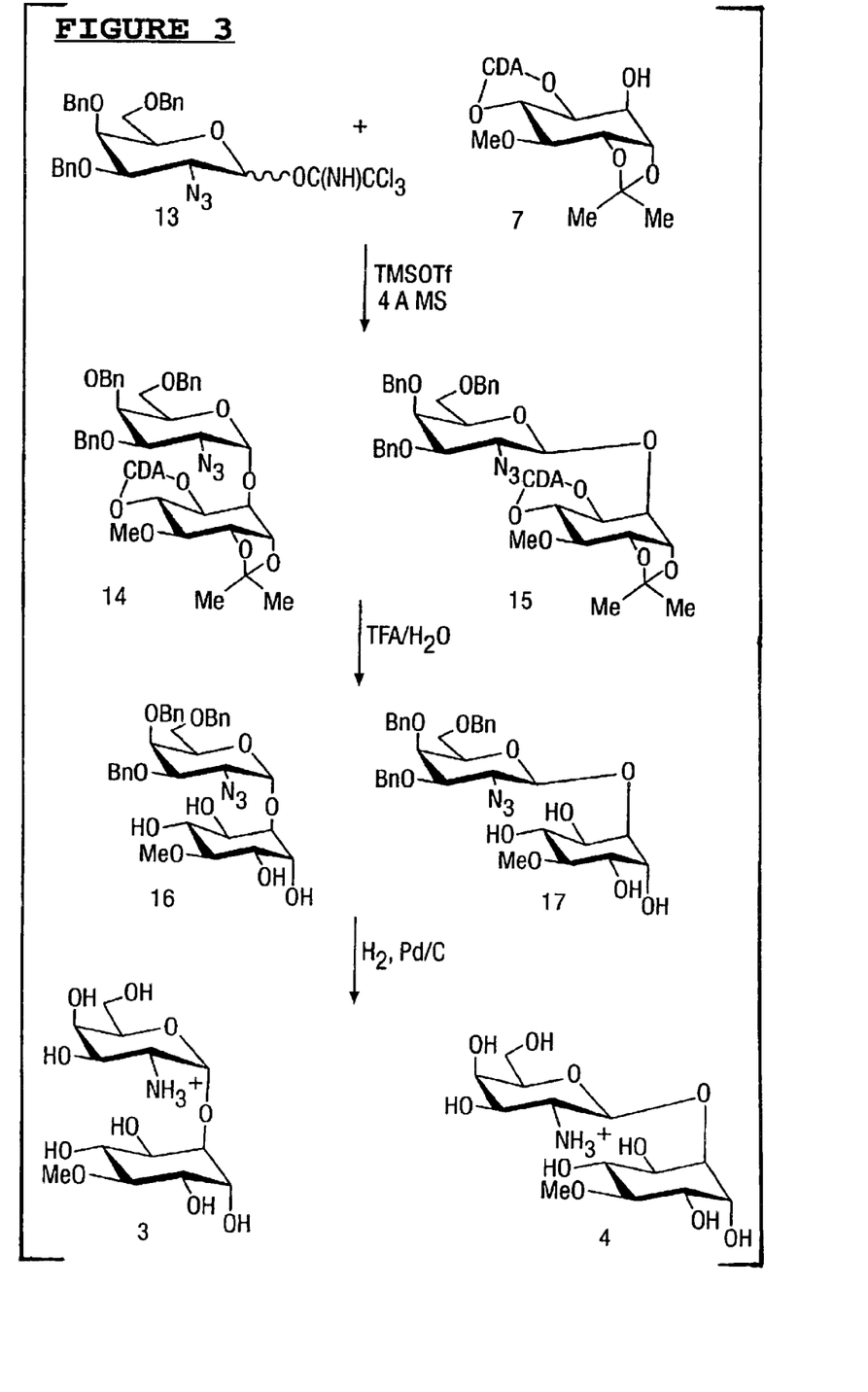
FIG. 3 shows a reaction scheme (Scheme 3) for the glycosylation of D-pinitol building block 7 with the 2-azido-2-deoxy-D-galactopyranosyl trichloroacetimidate 13 to give the IPG-like compounds 3 and 4.

Glycosylation of 7 with 2-azido-2-deoxy-3,4,6-tri-O-benzyl-D-galactopyranose (13) under different conditions gave a mixture of α- and β-linked pseudodisaccharides 14 and 15 in moderate yield (Scheme 3). Removal of the acetal groups and subsequent hydrogenolysis afforded 3 and 4.

4,5-O-(1',2'-dimethoxycyclohexane-1',2'-diyl)-3-O-methyl-D-chiro-inositol (6)

3-O-methyl-D-chiro-inositol (D-pinitol) (283 mg, 1.457 mmol, 1 equiv) was dissolved in methanol (15 mL), then 1,2-cyclohexane diacetal (507 mg, 2.458 mmol, 1.7 equiv), trimethyl orthoformate (200 mL, 1.752 mmol, 1.2 equiv) and 1-(S)-(+)-10-camphorsulfonic acid (24 mg, 0.102 mmol, 0.07 equiv) were added. The reaction mixture was heated at 70° C. for 24 h whereupon it was diluted with MeOH and quenched with solid $NaHCO_3$. The residue was concentrated and purified by flash chromatography (Hex/EtOAc 1.15) to give 6 (222 mg, 0.664 mmol, 45%; 89% based on 134 mg of recovered D-pinitol). $R_f$(Hex/EtOAc 1:20): 0.22; $[\alpha]^{20}_D$ –22.9 (c=1.05, $CHCl_3$); $^1H$ NMR ($CDCl_3$, 300 MHz): d=4.12 (Ys, 1H, $H_1$), 4 10 (s, 2H, $H_4$, $H_5$), 4.07 (Ys, 1H, $H_6$), 3.81 (dt, 1H, $J_{2-3}$=9.0 Hz, $J_{2-1}$=3.6 Hz, $J_{2-OH}$=1.8 Hz, $H_2$), 3.47 (t, 1H, J=9.0 Hz, $H_3$), 3.23 (s, 3H, $OCH_3$), 3.21 (s, 3H, $OCH_3$), 2.76 (d, 1H, $J_{OH-2}$=1.8 Hz, $OH_2$), 2.60 (s, 1H, $OH_1$), 2.56 (s, 1H, $OH_6$), 1.86–1.78 (m, 1H, CDA), 1.77–1.66 (m, 3H, CDA), 1.57–1.50 (m, 2H, CDA), 1.42–1.34 (m, 2H, CDA); $^{13}C$-NMR ($CDCl_3$, 75 MHz); d=98.9 (C), 98.0 (C), 80.2 ($C_3$), 71.5($C_2$), 70.8, 70.4, 70.3 ($C_1$, $C_4$, $C_6$), 68.7 ($C_5$), 61.1 ($OCH_3$), 47.0($OCH_3$, CDA), 46.8 ($OCH_3$, CDA), 27.1 ($CH_2$), 27.0 ($CH_2$), 21.5 ($CH_2$), 21.4 ($CH_2$); HRFABMS Calcd. for $C_{15}H_{26}O_8$: 357.3571. found; 357.1528. MALDI-TOF Calcd. for $C_{15}H_{26}O_8+Na^+$: 357.4. found: 357.5. calcd. for $C_{15}H_{26}O_8+K^+$: 373.5. found: 374.1.

4,5-O-(1',2'-dimethoxycyclohexane-1',2'-diyl)-3-O-methyl-1,2-O-isopropyliden-D-chiro-inositol (7)

4,5-O-(1',2'-dimethoxycyclohexane-1',2'-diyl)-3-O-methyl-D-chiro-inositol (6) (326 mg, 0.975 mmol, 1 equiv) and 2,2-dimethoxypropane (1,321 mL, 1.072 mmol, 1.1 equiv) in acetone (4 mL) were treated with p-toluenesulfonic acid monohydrate (9.3 mg, 0.049 mmol, 0.05 equiv). The reaction was stirred for 1 h, whereupon it was quenched with solid $NaHCO_3$, the solvent evaporated and the residue purified by flash chromatography (Hex/AcOEt 1:1) to give 7 (292 mg, 0.873 mmol, 81%) as a white solid. $R_f$ (Hex/tOAc 3:1): 0.71; $[\alpha]^{20}_D$ –18.0 (c=0.30, $CHCl_3$); $^1H$ NMR ($CDCl_3$, 500 MHz): d=4.27 (dd, 1H, $J_{1-2}$=7.3 Hz, $J_{1-6}$=3.2 Hz, $H_1$), 4.24 (t, 1H, J=3.2 Hz, $H_6$), 4.16 (t, 1H, J=7.3 Hz, $H_2$), 4.06 (t, 1H, J=10.2 Hz, $H_4$), 3.94 (dd, 1H, $J_{5-4}$=10.2 Hz, $J_{5-6}$=3.2 Hz, $H_5$), 3.61 (s, 3H, $OCH_3$), 3.39 (dd, 1H, $J_{3-4}$=10.2 Hz, $J_{3-2}$=7.3 Hz, $H_3$), 3.23 (s, 3H, $OCH_3$, CDA), 3.22 (s, 3H, $OCH_3$, CDA), 1.86–1.78 (m, 1H, CDA), 1.77–1.66 (m, 3H, CDA), 1.52 (s, 3H, $CH_3$), 1.57–1.51 (m, 2H, CDA), 1.36 (s, 3H, $CH_3$), 1.41–1.33 (m, 2H, CDA); $^{13}C$-NMR ($CDCl_3$, 125 MHz): d=109.0 (C), 98.4 (C, CDA), 97.8 (C, CDA), 82.7 ($C_3$), 79.6 ($C_2$), 76.4 ($C_1$), 68.5 ($C_5$), 68.3 ($C_6$), 67,4($C_4$), 60.2 ($OCH_3$), 47.1 ($OCH_3$, CDA), 46.9 ($OCH_3$, CDA), 27.0 ($CH_3$), 27.1 ($CH_2$), 26.9 ($CH_2$), 21.4 ($CH_2$); Anal. Calcd. for $C_{18}H_{30}O_8$: C, 57.74%; H, 8.08%. found: 57.46%; H, 7.86%. HRFABMS Calcd. for $C_{18}H_{30}O_8+Na^+$: 397.1338. found: 397.1854. MALDI-TOF Calcd. for $C_{18}H_{30}O_8+Na^+$: 397.4. found: 397.3. calcd. for $C_{18}H_{30}O_8+K^+$: 413.5. found: 413.8.

Glycosylation Reaction of 7 and 8

To a solution of 8 (809 mg, 1.305 mmol, 1.5 equiv) in $CH_2Cl_2$ (4 mL), compound 7 (295 mg, 0.788 mmol, 1 equiv) and freshly activated 4 Å molecular sieves were added and the mixture stirred for 1 h under Argon. Then, TMSOTf (12.6 mL, 0.104 mmol, 0.08 equiv) was added and the reaction mixture stirred for 24 h. The suspension was filtered through celite and the solvent evaporated under vacuum to provide a mixture of two disaccharides (α/β=2:1) which can be separated by flash chromatography (Hex/EtOAc 4:1) to obtain 9 (235 mg, 0.282 mmol, 36%) and 10 (118 mg, 0.142 mmol, 18%).

2-Azido-2-deoxy-3,4,6-tri-O-benzyl-D-glucopyranosyl-α(1-6)-4,5-O-(1',2'-dimethoxycyclohexane-1',2'-diyl)-1,2-O-isopropyliden-3-O-methyl-D-chiro-inositol (9)

Rf(Hex/EtOAc 3:1): 0.17; $[\alpha]^{20}_D$ +48.8° (c=0.25, $CHCl_3$); $^1H$ NMR ($CDCl_3$, 500 MHz): d=7.43–7.22 (m, 15H, Ph), 4.94 (d, 1H, $J_{1'-2'}$=3.2 Hz, $H_{1'}$), 4.83 (d, 1H, J=13.0 Hz, CHPh), 4.82 (AB syst., 2H, $CH_2Ph$), 4.58 (d, 1H, J=12.0 Hz, CHPh), 4.58 (m, 1H, $H_{5'}$), 4.57 (d, 1H, J=13.0 Hz, CHPh), 4.42 (d, 1H, J=12.0 Hz, CHPh), 4.25 (t, 1H, J=6.4 Hz, $H_2$), 4.18 (t, 1H, J=2.5 Hz, $H_1$), 4.16 (t, 1H, J=2.5 Hz, $H_6$), 4.11 (t, 1H, J=10.5 Hz, $H_4$), 3.96 (t, 1H, J=10.1 Hz, $H_{3'}$), 3.90 (dd, 1H, $J_{5-4}$=10.5 Hz, $J_{5-6}$=2.5 Hz, $H_5$), 3.79 (t, 1H, J=10.1 Hz, $H_{4'}$), 3.71 (dd, 1H, $J_{6a'-6b'}$=10.8 Hz, $J_{6a'-5'}$=2.4 Hz, $H_{6a'}$), 3.60 (s, 3H, $OCH_3$), 3.59 (dd, 1H, $J_{6a'-6b'}$=10.8 Hz, $J_{6b'-5'}$=1.6 Hz, $H_{6b'}$), 3.41 (dd, 1H, $J_{3-4}$=10.5 Hz, $J_{3-2}$=6.4 Hz, $H_3$), 3.36 (dd, 1H, $J_{2'-3'}$=10.2 Hz, $J_{2'-1'}$=3.2 Hz, $H_{2'}$), 3.19 (s, 6H, 2 $OCH_3$, CDA), 1.83–1.78 (m, 1H, CDA), 1.72–1.61 (m, 3H, CDA), 1.52 (s, 3H, $CH_3$), 1.55–1.43 (m, 2H, CDA), 1.40–1.30 (m, 2H, CDA), 1.36 (s, 3H, $CH_3$); MALDI-TOF Calcd. for $C_{45}H_{57}N_3O_{12}+Na^+$: 855.0. found: 854.3. calcd. for $C_{45}H_{57}N_3O_{12}+K^+$: 871.1. found: 870.5.

2-Azido-2-deoxy-3,4,6-tri-O-benzyl-D-glucopyranosyl-β(1-6)-4,5-O-(1',2'-dimethoxycyclohexane-1',2'-diyl)-1,',2'-O-isopropyliden-3-O-methyl-D-chiro-inositol (10)

$R_f$ (Hex/EtOAc3:1): 0.20; $[\alpha]^{20}_D$ –8.0° (c=1.18, $CHCl_3$); $^1H$ NMR($CDCl_3$, 500 MHz): d 7.40–7.24 (m, 13H, Ph), 7.21–7.13 (m, 2H, Ph), 4.97 (d, 1H, $J_{1'-2'}$=8.1 Hz, $H_{1'}$), 4.92 (d, 1H, J=10.8 Hz, CHPh), 4.82 (d, 1H, J=10.8 Hz, CHPh), 4.78 (d, 1H, J=10.8 Hz, CHPh), 4.62 (d, 1H, J=10.8 Hz, CHPh), 4.58 (AB syst., 2H, $CH_2Ph$), 4.49 (t, 1H, J=2.5 Hz, $H_{6'}$), 4.30 (dd, 1H, $J_{1-2}$=5.1 Hz, $J_{1-6}$=2.5 Hz, $H_1$), 4.20 (t, 1H, J=10.8 Hz, $H_4$), 4.17 (t, 1H, J=5.1 Hz, $H_2$), 3.98 (dd, 1H, $J_{5-4}$=10.8 Hz, $J_{5-6}$=2.5 Hz, $H_5$) 3.71–3 57 (m, 3H, $H_{5'}$, $H_{6'}$, $H_{4'}$), 3.61 (s, 3H, $OCH_3$), 3.47–3.39 (m, 3H, $H_{3'}$, $H_3$, $H_{6'}$), 3.30 (dd, 1H, J=8.1 Hz, $H_{2'}$), 3.23 (s, 3H, $OCH_3$, CDA), 3.18 (s, 3H, $OCH_3$, CDA), 1.83–1.77 (m, 1H, CDA), 1.80–1.43 (m, 5H, CDA), 1.52 (s, 3H, $CH_3$), 1.41–1.28 (m, 2H, CDA), 1.33 (s, 3H, $CH_3$); $^{13}C$-NMR ($CDCl_3$, 125 MHz): d=138.5 (C), 138.4 (C), 138.3 (C), 128 9 (2CH), 128.8 (2CH), 128.8 (CH), 128.8 (2CH), 128.4 (2CH), 128.3 (2CH), 128.3 (CH), 128.2 (2CH), 128.1 (CH), 109.9 (C), 101.3 ($C_{1'}$), 98.4 (C, CDA), 98.0 (C, CDA), 83.9 ($C_{3'}$), 83.6 ($C_3$), 78.1 ($C_{4'}$), 76.7 ($C_1$), 76.0 ($CH_2$), 75.9 ($C_{6'}$), 75.5 ($CH_2$), 75.4 ($CH_2$), 73.9 ($C_6$), 72.6 ($C_5$), 68.8 ($C_5$), 68.7 ($C_2$), 68.1 ($C_4$), 67.5 ($C_{2'}$), 60.4 ($OCH_3$), 47.4 ($OCH_3$, CDA), 47.3 ($OCH_3$, CDA), 28.4 ($CH_3$), 27.5 ($CH_2$), 27.4 ($CH_2$), 26.3 ($CH_3$), 21.8 (2$CH_2$); HRFABMS Calcd. for $C_{45}H_{57}N_3O_{12}$: 854.3840. found= 854.3872. MALDI-TOF Calcd. for $C_{45}H_{57}N_3O_{12}+Na^+$: 855.0. found: 854.3. calcd. for $C_{45}H_{57}N_3O_{12}+K^+$: 871.1. found: 870.4.

2-Azido-2-deoxy-3,4,6-tri-O-benzyl-D-galactopyranosyl-α(1-6)-4,5-O-(1',2'-dimethoxycyclohexane-1,',2'-diyl)-1,2-O-isopropyliden-3-O-methyl-D-chiro-inositol (14)

To a solution of 13 (84 mg, 0.14 mmol, 1.3 equiv), 7 (39 mg, 0.10 mmol, 1.0 equiv) in $CH_2Cl_2$:Hex, 1:3 (2 mL) and freshly activated 4 Å molecular sieves were added and the mixture stirred for 1 h under Argon. Then, TMSOTf (2.43 mL, 0.02 mmol, 0.15 equiv) was added at $-40°$ C. and the reaction mixture stirred for 24 h at $0°$ C. The suspension was filtered through celite and the solvent removed under vacuum to provide the crude material. Flash chromatography (Hex/EtOAc 4:1) afforded 14 (38 mg, 0.046 mmol, 46%). $R_f$ (Hex/EtOAc 1:1): 0.67; $[\alpha]^{20}_D$ +59.7° (c=1.44, $CHCl_3$); $^1H$ NMR ($CDCl_3$, 300 MHz): d=7.46–7.28, (m, 15H, Ph), 4.98 (d, 1H, J=3.3 Hz, $H_{1'}$), 4.89 (d, 1H, J=11.2 Hz, CHPh), 4.78 (d, 1H, J=11.1 Hz, CHPh), 4.69 (m, 1H, $H_{5'}$), 4.67 (d, 1H, J=11.1 Hz, CHPh), 4.59 (d, 1H, J=11.2 Hz, CHPh), 4.46, (AB syst., 2H, $CH_2Ph$), 4.28 (t, 1H, J=6.3 Hz, $H_2$), 4.20 (m, 2H, $H_1$, $H_6$), 4.15 (bs, 1H, $H_{4'}$), 4.11 (m, 1H, $H_4$), 4.04 (dd, 1H, $J_{3'-2'}$=10.6 Hz, $J_{3'-4'}$=2.4 Hz, $H_{3'}$), 3.92 (dd, 1H, $J_{4-5}$=10.8 Hz, $J_{5-6}$=2.1 Hz, $H_5$), 3.86 (dd, 1H, $J_{2'-3'}$=10.6 Hz, $J_{2'-1'}$=3.3 Hz, $H_{2'}$), 366–3.60 (m, 1H, $H_{6b'}$), 3.63 (s, 3H, $OCH_3$), 3.50 (dd, 1H, $J_{6a'-6b'}$=8.1 Hz, $J_{6a'-5'}$=5.4 Hz, $H_{6a'}$), 3.42 (dd, 1H, $J_{3-4}$=10.2 Hz, $J_{3-2}$=6.3 Hz, $H_3$), 3.20 (s, 3H, $OCH_3$, CDA), 3.18 (s, 3H, $OCH_3$, CDA), 1.90–1.63 (m, 4H, CDA), 1.54 (s, 3H, $CH_3$), 1.60–1.33 (m, 4H, CDA), 1.40 (s, 3H, $CH_3$); $^{13}C$-NMR ($CDCl_3$, 75 MHz): δ 139.0 (C), 138.5 (C), 138.0 (C), 110 2 (C), 98.3 (C, CDA), 98.2 (C, CDA), 97.8 ($C_{1'}$), 83.6 ($C_3$), 80.6 ($C_2$), 77.2 ($C_{3'}$), 75.2 ($C_6$), 75.0 ($CH_2$), 73.9 ($C_{4'}$), 73.8 ($CH_2$), 72.8 ($C_1$), 72.7 ($CH_2$), 69.9 ($C_{5'}$), 68.4 ($C_{6'}$), 68.1 ($C_4$), 67.1 ($C_5$), 60.5 ($OCH_3$), 60.0 ($C_{2'}$), 47.2 ($2OCH_3$, CDA), 28.5 ($CH_3$), 27.4 ($CH_2$), 27.0 ($CH_2$), 26.7 ($CH_3$), 21.9 (2 $CH_2$); MALDI-TOF Calcd. for $C_{45}H_{57}N_3O_{12}+Na^+$: 855.0. Found: 854.0. Calcd. for $C_{45}H_{57}N_3O_2+K^+$: 871.1. Found: 870.1.

2-Azido-2-deoxy-3,4,6-tri-O-benzyl-D-glucopyranosyl-α (1-6)-3-O-methyl-D-chiro-inositol (11)

Disaccharide (9) was dissolved in a mixture of trifluoroacetic acid/water (20:1, 3.7 mL) and stirred at room temperature for 40 min. Then, the reaction mixture was diluted with $CH_2Cl_2$ (10 mL) and immediately poured into an ice-cold, vigorously stirred solution of saturated aqueous sodium bicarbonate (90 mL). The layers were separated, and the aqueous phase extensively extrated ($CH_2Cl_2$, 4×30 ml), dried over $Na_2SO_4$ and concentrated under vacuum. Purification by flash chromatography ($Cl_2CH_2$/MeOH, 11:1 and then $CH_2Cl_2$/MeOH, 15:1) afforded 11 (4 mg, 6.138 mmol, 56%). $R_f$ ($Cl_2CH_2$/MeOH, 9:1); 0.3; $[\alpha]^{20}_D$ +38.5° (c=0.19, $CHCl_3$); $^1H$ NMR ($CDCl_3$, 500 MHz): d=7.34–7.16 (m, 15, Ph), 4.94 (d, 1H, J=3.5 Hz, $H_1$), 4.84 (AB syst., 2H, $CH_2Ph$), 4.79 (d, 1H, J=11.0 Hz, CHPh), 4.56 (d, 1H, J=11.0 Hz, CHPh), 4.50 (d, 1H, J=11.0 Hz, CHPh), 4.47 (d, 1H, J=11.0 Hz, CHPh), 4.16 (bs, 1H, $H_1$), 4.12 (m, 1H, $H_{5'}$), 4.04 (bs, 1H, $H_6$), 3.92 (m, 1H, $H_2$), 3.87–3.84 (m, 2H, $H_{3'}$, $H_5$), 3.71 (Yt, 1H, J=8.0 Hz, $H_4$), 3.56 (m, 3 H, $H_{4'}$, $2H_{6'}$), 3.63 (s, 3H, $OCH_3$), 3.44 (dd, 1H, $J_{2'-3'}$=10.0 Hz, $J_{1'-2'}$=3.5 Hz, $H_{2'}$), 3.37 (Yt, 1H, J=8.0 Hz, $H_3$).

2-Azido-2-deoxy-3,4,6-tri-O-benzyl-D-glucopyranosyl-β (1-6)-3-O-methyl-D-chiro-inositol (12)

Compound 12 (28 mg, 43.0 mmol, 71%) was obtained via the general procedure described above for compound 11. Purification by flash chromatography (Hex/EtOAc 1:20). $R_f$ (EtOAc): 0.47; $^1H$ NMR ($CDCl_3$, 500 MHz): d=7.34–7.26 (m, 13H, Ph), 7.19–7.10 (m, 2H, Ph), 4.83 (AB syst., 2H, $CH_2Ph$), 4.78 (d, 1H, J=11.0 Hz, CHPh), 4.54 (AB syst., 2H, $CH_2Ph$), 4.52 (d, 1H, J=11.0 Hz, CHPh), 4.46 (d, 1H, J=8.0 Hz, $H_1$), 4.21 (bs, 1H, $H_1$), 4.10 (bs, 1H, $H_6$), 3.94–3.90 (m, 2H, $H_5$), 3.80 (t, 1H, J=8.5 Hz, $H_4$), 3.69–3.59 (m, 2H, $2H_{6'}$), 3.62 (s, 3H, $OCH_3$), 3.58 (t, 1H, J=9.5 Hz, $H_{4'}$), 3.47 (t, 1H, J=9.5 Hz, $H_3$), 3.46–3.36 (m, 3H, $H_{2'}$, $H_{5'}$, $H_3$), 3.35–3.27 (bs, 1H, OH), 3.27–3.15 (bs, 1H, OH), 3.15–2.94 (2bs, 2H, 2OH).

2-Azido-2-deoxy-3,4,6-tri-O-benzyl-D-galactopyranosyl-α (1-6)-3-O-metbyl-D-chiro-inositol (16)

Compound 16 (7 mg, 10.7 mmol, 41%) was obtained via the general procedure described above for compound 11, using purification by flash chromatography ($CH_2Cl_2$/MeOH, 10:1). $R_f$ ($CH_2Cl_2$/MeOH 9:1): 0.48; $^1H$ NMR ($CDCl_3$, 500 MHz): d=7.36–7.21 (m, 15H, Ph), 4.96 (d, 1H, $J_{1-2}$=3.5 Hz, $H_{1'}$), 4.85 (d, 1H, J=11.5 Hz, CHPh), 4.71 (d, 1H, J=11.0 Hz, CHPh), 4.67 (d, 1H, J=11.0 Hz, CHPh), 4.49 (d, 1H, J=11.0 Hz), 4.49 (d, 1H, J=11.5 Hz, CHPh), 4.40 (d, 1H, J=11.0 Hz, CHPh), 4.20 (dd, 1H, $J_{4'-5'}$=7.5 Hz, $J_{5'-6'}$=4.5 Hz, $H_{5'}$), 4.15 (t, 1H, J=4.0 Hz, $H_1$), 4.01 (t, 1H, J=4.0 Hz, $H_6$), 3.95–3.90 (m, 2H, $H_{2'}$, $H_{4'}$), 3.87 (m, 1H, $H_2$), 3.84 (dd, $J_{2'-3'}$=10.5 Hz, $J_{3'-4'}$=2.5 Hz, $H_{3'}$), 3.82–3.77 (m, 1H, $H_5$), 3.65 (t, 1H, J=8.2 Hz, $H_4$), 3.62 (s, 3H, $OCH_3$), 3.58 (dd, 1H, $J_{6a'-6b'}$=9.5 Hz, $J_{5'-6a'}$=7.5 Hz, $H_{6a'}$), 3,38 (dd, 1H, $J_{6a'-6b'}$=9.5 Hz, $J_{5'-6b'}$=4.5 Hz, $H_{6b'}$), 3.35 (t, 1H, J=8.2 Hz, $H_3$).

2-Amino-2-deoxy-D-glucopyranosyl-α(1-6)-3-O-methyl-D-chiro-inositol (1)

Compound 11 (3.8 mg, 5.831 mmol, 1.0 equiv) and 10% Pd/C (10 mg, 9.398 mmol) were stirred in methanol under a hydrogen atmosphere for 24 h. The slurry was filtered, washed with water and the filtrate was concentrated and lyophilized to give the fully deprotected disaccharide 1 (2.6 mg, 7.3 mmol, quantitative). $R_f$ (EtOAc/MeOH/$H_2O$/AcOH 2:2:1:1): 0.44; $[\alpha]^{20}_D$ +55.2° (c=0.125, $H_2O$), $^1H$ NMR ($D_2O$, 500 MHz) δ=5.22 (d, 1H, $H_{1'}$), 4.16 (t, 1H, $H_1$), 4.19 (t, 1H, $H_6$), 4.07 (dt, 1H, $H_5$), 3.90 (dd, 1H, $H_5$), 3.85–3.75 (m, 3H, $H_{4'}$, $H_{6a'}$, $H_{6b'}$), 3.80 (dd, 1H, $H_2$), 3.70 (t, 1H, $H_{3'}$), 3.64 (s, 3H, $OCH_3$), 3.52 (t, 1H, $H_4$), 3.36 (t, 1H, $H_3$), 3.24 (dd, 1H, $H_{2'}$).

2-Amino-2-deoxy-1)-glucopyranosyl-β(1-6)-3-O-Methyl-D-chiro-inositol (2)

Compound 12 (24 mg, 67.54 mmol, 98%) was treated as described above to afford compound 2. $R_f$ (EtOAc/MeOH/$H_2O$/AcOH 2:2:1:1): 0.42, $^1H$ NMR ($D_2O$, 500 MHz), d=4.70 (d, 1H, J=8.5 Hz, $H_1$), 4.32 (Yt, 1H, J=3.5 Hz, $H_1$), 4.12 (Yt, 1H, J=35 Hz, $H_6$), 3.96 (dd, 1H, $J_{6a'-6b'}$=9.5 Hz, $J_{6a'-5'}$=1.7 Hz, $H_{6a'}$), 3.92 (dd, 1H, $J_{5-4}$=8.5 Hz, $J_{5-6}$=3.5 Hz, $H_5$), 3.88 (dd, 1H, $J_{2-3}$=9.8 Hz, $J_{1-2}$=6.6 Hz, $H_2$), 3.82 (dd, 1H, $J_{6a'-6b'}$=9.5 Hz, $J_{5'-6b'}$=4.0 Hz, $H_{6b'}$), 3.78 (t, 1H, J=9.5 Hz, $H_{4'}$), 3.66 (s, 3H, $OCH_3$), 3.48 (t, 1H, J=9.8 Hz, $H_{4'}$), 3.57–3.51 (m, 2H, $H_{3'}$, $H_5$), 3.40 (t, 1H, J=9.8 Hz, $H_3$), 2.86 (t, 1H, J=8.5 Hz, $H_2$).

2-Amino-2-deoxy-D-glucopyranosyl-α(1-6)-3-O-methyl-D-chiro-inositol (14)

Compound 14 (5.3 mg, 14.9 mmol, quantitative) was obtained via the general procedure described above for compound 12. $R_f$ ($Cl_2CH_2$/MeOH 9/1): 0.071; $[\alpha]^{20}_D$ (c=0.305, $H_2O$): +70.1; $^1H$ NMR ($D_2O$, 500 Mz): δ=5.31 (d, 1H, J=3.5 Hz, $H_1$), 4.29 (t, 1H), 4.19 (Ψt, 1H, $H_1$), 4.14 (Ψt, 1H, $H_6$), 4.05 (Ψs, 1H, $H_{4'}$), 3.92 (dd, 1H), 3.77 (d, 3H), 3.72 (t, 1H), 3.65 (s, 3H, $OCH_3$)3.62 (m, 1H), 3.52 (dd, 1H, $J_{2'-3'}$=11.0 Hz, $J_{1'-2'}$=3.5 Hz, $H_{2'}$), 3.37 (t, 1H, J=10.0 Hz, $H_3$).

Assay Data

| PDH % activation: | |
|---|---|
| | 100 μM |
| RGL1015 | 38% |
| RGL1024 | 65% |

-continued

PDH % activation:

|  | 100 μM |
|---|---|
| RGL1025 | 17% |

PKA % inhibition:

|  | 0.1 μM | 1 μM | 10 μM |
|---|---|---|---|
| RGL1015 | 14% | 15% | — |
| RGL1024 | 17% | 34% | 2% |
| RGL1025 | 48% | −13% | — |

Figure 4:
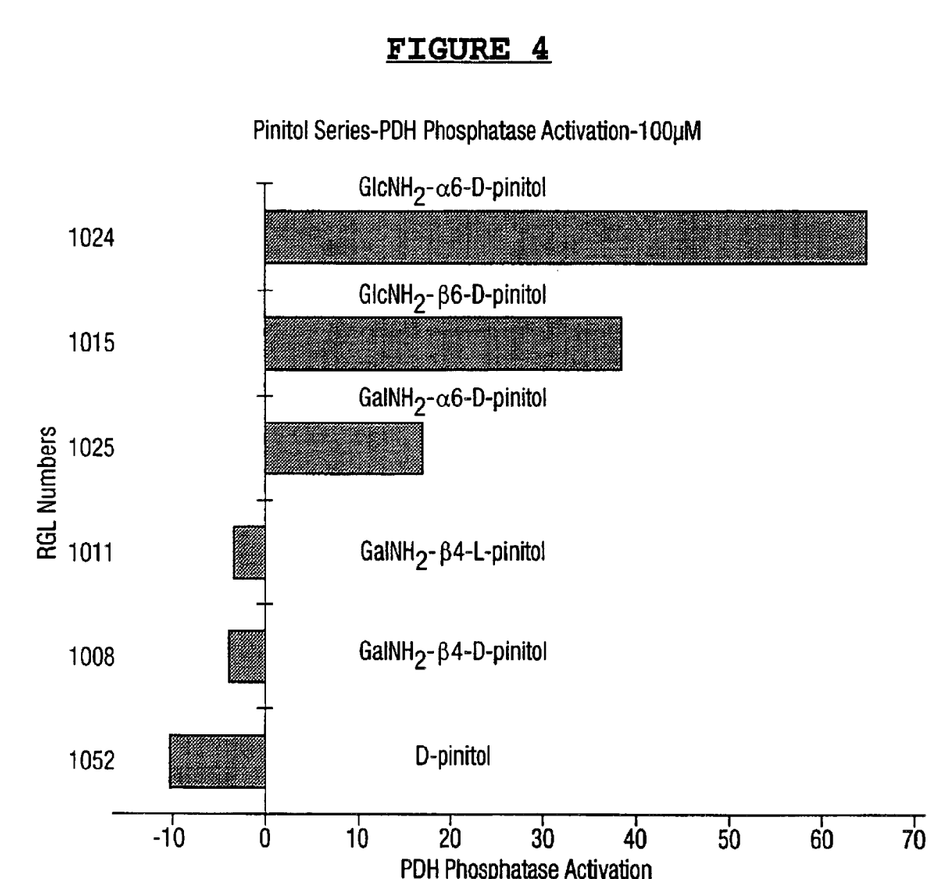
FIG. 4 is a graph showing the PDH phosphatase activation of exemplary compounds of the invention as compared to D-pinitol.

FIG. 4 shows a graphical comparison of PDH phosphatase activation at 100 μM of compounds of the invention as compared to D-pinitol. In particular, preferred compounds having 1,6 linkages are good activators of PDH phosphatase activity.

REFERENCES

The references mentioned herein are all expressly incorporated by reference.

[1] (a) Varela-Nieto et al, *Comp. Biochem. Physiol.*, 115B:223–241, 1996; (b) Strälfors, *Bioassays*, 19:327–335, 1997; (c) Field, *Glycobiology*, 7:161–168, 1997; (d) Jones & Varela-Nieto, *Int. J. Biochem. Cell Biol.*, 30:313–326, 1998.
[2] Mato et al, *Biochem. Biophys. Res. Commun.*, 146:746–770, 1987.
[3] Larner et al, *Biochem. Biophys. Res. Commun.*, 151:1416–1426, 1998.
[4] Caro et al, *Biochem. Mol. Med.*, 61:214–228, 1997.
[5] For reviews on the synthesis of these structures see: (a) Gigg & Gigg in *Glycopeptides and Related Compounds*, Large & Warren, Eds., Marcel Dekker, New York, 1997, pp 327–392; (b) Khiar & Martin-Lomas in *Carbohydrate Mimics. Concepts and Methods*, Chapleur Ed Wiley VCH, 1998, pp 443–462; (c) Dietrich et al, *Chem. Eur J*, 5:320–336, 1999.
[6] Jaramillo et al, *J. Org. Chem.*, 59,3135–3141, 1994.
[7] Corey & Venkateswarlu, *J. Am. Chem. Soc.*, 94:6190, 1974
[8] Ley et al, *Angew. Chem. Chem. Int. Ed. Engl.*, 33:2290–2292, 1994.
[9] Kinzi & Schmidt, *Liebigs Ann. Chem.*, 1537–1545, 1985.
[10] Vasella et al, *Helv. Chim. Acta.*, 74:2073–2077, 1991
[11] Schmidt & Kinzi, *Adv. Carbohydy. Chem. Biochem.*, 50:21–123, 1994.
[12] Once et al, *Chem. Eur. J.*, 3:431–440, 1997.
[13] Rademacher et al, *Brazilian J. Med. Biol. Res.*, 27:327–341, 1994.
[14] Caro et al, *Biochem. Molec. Med.*, 61:214–228, 1997.
[15] Kunjara et al, In: Biopolymers and Bioproducts: Structure, Function and Applications, Ed Svati et al, 301–305, 1995.
[16] Baeschlin et al, *Chem. Eur. J.*, 6(1):172–186, 2000.
WO98/11116 and WO98/11117 (Rademacher Group Limited).
WO98/11435 and WO98/10791 (Rademacher Group Limited).
WO99/38516 (Rademacher Group Limited).

We claim:

1. A compound represented by the general formula:

X-β1,6-pinitol wherein,
X represents a sugar residue;
the sugar residue is substituted with one, two or three groups, and the pinitol is unsubstituted or is further substituted with between one and four groups, said substituted groups being substituted on at least one of said sugar residue and said pinitol and being independently selected from the group consisting of:
(a) a phosphoryl group having a formula selected from the group consisting of —O—P(O)(OH)$_2$, —O—P(S)(OH)$_2$, —O—P(O)(OR)$_2$, —O—P(S)(OR)$_2$, —O—P(O)OHR, —O—P(S)OHR, —O—P(O)OR$_1$R$_2$, —O—P(S)OR$_1$R$_2$, —O—P(S)(OH)(SH), or a cyclic phosphate;
(b) a phosphorus-containing group having a formula selected from the group consisting of —O—P(OR)—NR$_1$R$_2$ and —O—P(O)(OR)—NR$_1$R$_2$;
(c) a sulphur-containing group having a formula selected from the group consisting of —O—S(O)(OH)$_2$, —SH, —SR, —S(—O)—R, —S(O)$_2$R, RO—S(O)$_2$$^-$, —O—SO$_2$NH$_2$, —O—SO$_2$R$_1$R$_2$ or —NHSO$_2$NH$_2$;
(d) a substituted amino-containing group having a formula selected from the group consisting of —NHR, —NR$_1$R$_2$, —NHAc, —NHCOR, —NH—O—COR, —NHSO$_3$$^-$, —NHSO$_2$R, —N(SO$_2$R), —NHC(═NH)NH$_2$, —NH—CO—NR$_1$R$_2$ or —NH—C(S)—NH$_2$;
(e) a hydroxy group; a substituted hydroxy group represented by the formula —OR$_3$, where R$_3$ is C$_{1-10}$ unsubstituted alkyl or C$_{1-10}$ substituted alkyl, alkoxyalkyl, aryloxyalkyl, cycloalkyl, alkenylalkyl in which the alkyl group is unsubstituted, alkylenecycoalkyl in which the cycloalkyl group has 3–7 carbon atoms, —OCOR, aryl, heteroaryl, acetal, or said substituted groups comprise two hydroxyl groups that are joined to form a ketal;
(f) halogen substituents fluorine or chlorine; and
(g) hydrogen, forming a deoxy sugar;
wherein R, R$_1$ and R$_2$ are independently hydrogen or C$_{1-10}$ unsubstituted alkyl or C$_{1-10}$ substituted alkyl or aryl;
or a derivative of the compound, said derivative comprising salts, coordination complexes with metal ions, esters, free acids or bases, hydrates or protecting groups.

2. The compound of claim 1, wherein the sugar residue is unsubstituted hexose or a pentose or said substituted forms thereof.

3. The compound of claim 2, wherein the sugar residue is a hexose selected from the group consisting of glucose, galactose or mannose.

4. The compound of claim 2, wherein the sugar residue is a hexosamine.

5. The compound of claim 4, wherein the hexosamine is galactosamine or glucosamine.

6. The compound of claims 1, wherein the sugar residue and the pinitol are α-linked.

7. The compound of claim 1, wherein the sugar residue and the pinitol are β-linked.

8. The compound of claim 1, wherein the pinitol is L-pinitol.

9. A compound selected from the group consisting of: O-(2-amino-2-deoxy-glucopyranosyl)-β(1,6)-D-3-O- methyl-chiro-inositol; O-(2-amino-2-deoxy-D-glucopyranosyl)-α(1,6)-D-3-O-methyl-chiro-inositol; O-(2-amino-2-deoxy-D-galactopyranosyl)-α(1,6)-D-3-O-methyl-chiro-inositol; and 1'-D-6-O-(2'-amino-2'-deoxy-β-D-galactopyranosyl)-3-O-methyl-D-chiro-inositol; or a derivative of said compound, said derivative comprising salts, coordination complexes with metal ions, free acids or bases, hydrates or protecting groups.

10. A composition comprising a compound of claim 1 in combination with a pharmaceutically acceptable carrier.

11. The compound of claim 1, wherein the pinitol is D-pinitol.

12. The compound of claim 1, wherein said substituted hydroxy group is $OR_3$ and $R_3$ is selected from the groups consisting of $CHF_2$ and $CF_3$.

13. The compound of claim 1, wherein said derivative is a coordination complex with a metal ion selected from the group consisting of Mn(+2) and Zn(+2).

14. A compound represented by the general formula:

X-β1,6-pinitol wherein:

X represents a sugar residue;

the sugar residue is substituted with between one and four groups, and the pinitol is further substituted with one, two or three groups, said substituted groups being substituted on at least one of said sugar residue and said pinitol and being independently selected from the group consisting of:

(a) a phosphoryl group having a formula selected from the group consisting of —O—P(O)(OH)$_2$, —O—P(S)(OH)$_2$, —O—P(O)(OR)$_2$, —O—P(S)(OR)$_2$, —O—P(O)OHR, —O—P(S)OHR, —O—P(O)$_0$R$_1$R$_2$, —O—P(S)OR$_1$R$_2$, —O—P(S)(OH)(SH), or a cyclic phosphate;

(b) a phosphorus-containing group having a formula selected from the group consisting of —O—P(OR)—NR$_1$R$_2$ and —O—P(O)(OR)—NR$_1$R$_2$;

(c) a sulphur-containing group having a formula selected from the group consisting of —O—S(O)(OH)$_2$, —SH, —SR, —S(—O)—R, —S(O)$_2$R, RO—S(O)$_2$⁻, —O—SO$_2$NH$_2$, —O—SO$_2$R$_1$R$_2$ or —NHSO$_2$NH$_2$;

(d) a substituted amino-containing group having a formula selected from the group consisting of —NHR, —NR$_1$R$_2$, —NHAc, —NHCOR, —NH—O—COR, —NHSO$_3$⁻, —NHSO$_2$R, —N(SO$_2$R), —NHC(=NH)NH$_2$, —NH—CO—NR$_1$R$_2$ or —NH—C(S)—NH$_2$;

(e) a hydroxy group; a substituted hydroxy group represented by the formula —OR$_3$, where R$_3$ is C$_{1-10}$ unsubstituted akyl or C$_{1-10}$ substituted alkyl, alkoxyalkyl, aryloxyalkyl, cycloalkyl, alkenylalkyl in which the alkyl group is unsubstituted, alkylene-cycoalkyl in which the cycloalkyl group has 3–7 carbon atoms, —OCOR, aryl, heteroaryl, acetal, or said substituted groups comprise two hydroxyl groups that are joined to form a ketal;

(f) halogen substituents fluorine or chlorine; and (g) hydrogen, forming a deoxy sugar;

wherein R, R$_1$, and R$_2$ are independently hydrogen or C$_{1-10}$ unsubstituted alkyl or C$_{1-10}$ substituted alkyl or aryl;

or a derivative of the compound, said derivative comprising salts, coordination complexes with metal ions, esters, free acids or bases, hydrates or protecting groups.

15. The compound of claim 14, wherein the sugar residue is unsubstituted hexose or pentose or said substituted form thereof.

16. The compound of claim 15, wherein the sugar residue is a hexose selected from the group consisting of glucose, galactose or mannose.

17. The compound of claim 15, wherein the sugar residue is a hexosamine.

18. The compound of claim 17, wherein the hexosamine is galactosamine or glucosamine.

19. The compound of claim 14, wherein the sugar residue and the pinitol are α-linked.

20. The compound of claim 14, wherein the sugar residue and the pinitol are β-linked.

21. The compound of claim 14, wherein the pinitol is L-pinitol.

22. A compositions comprising a compound of claim 14 in combination with a pharmaceutically acceptable carrier.

23. The compound of claim 14, wherein the pinitol is D-pinitol.

24. The compound of claim 14, wherein said substituted hydroxy group is OR$_3$ and R$_3$ is selected from the groups consisting of CHF$_2$ and CF$_3$.

25. The compound of claim 14, wherein said derivative is a coordination complex with a metal ion selected from the group consisting of Nn(+2) and Zn(+2).

* * * * *